US010052025B2

(12) United States Patent
Haveri

(10) Patent No.: US 10,052,025 B2
(45) Date of Patent: Aug. 21, 2018

(54) SENSOR, GAS ANALYZER AND METHOD FOR MEASURING CONCENTRATION OF AT LEAST ONE RESPIRATORY GAS COMPONENT

(71) Applicant: GE Healthcare Finland OY, Helsinki (FI)

(72) Inventor: Heikki Antti Mikael Haveri, Huhmari (FI)

(73) Assignee: GE HEALTHCARE FINLAND OY, Helsinki (FI)

( * ) Notice: Subject to any disclaimer, the term of this patent is extended or adjusted under 35 U.S.C. 154(b) by 362 days.

(21) Appl. No.: 13/849,578

(22) Filed: Mar. 25, 2013

(65) Prior Publication Data
US 2013/0253336 A1 Sep. 26, 2013

(30) Foreign Application Priority Data
Mar. 26, 2012 (EP) ..................... 12161189

(51) Int. Cl.
A61B 5/083 (2006.01)
A61B 5/087 (2006.01)
(Continued)

(52) U.S. Cl.
CPC ............ *A61B 5/0075* (2013.01); *A61B 5/082* (2013.01); *A61B 5/0836* (2013.01);
(Continued)

(58) Field of Classification Search
CPC .................................................. A61B 5/082
See application file for complete search history.

(56) References Cited

U.S. PATENT DOCUMENTS

| 4,914,720 A | * | 4/1990 | Knodle | A61B 5/097 |
| | | | | 250/252.1 |
| 2005/0076904 A1 | * | 4/2005 | Jones | A61M 15/009 |
| | | | | 128/200.23 |
| 2007/0039466 A1 | * | 2/2007 | Nawata | A61M 16/10 |
| | | | | 95/96 |
| 2007/0225612 A1 | | 9/2007 | Mace et al. | |
| 2007/0274693 A1 | * | 11/2007 | Farbarik | A61M 16/0051 |
| | | | | 388/806 |
| 2008/0228096 A1 | * | 9/2008 | Jaffe | A61B 5/0836 |
| | | | | 600/532 |
| 2009/0227887 A1 | * | 9/2009 | Howard | A61B 5/0833 |
| | | | | 600/531 |

(Continued)

FOREIGN PATENT DOCUMENTS

| EP | 0512535 A2 | 11/1992 | |
| EP | 0733341 A2 | * 9/1996 | ........... A61B 5/0836 |

(Continued)

OTHER PUBLICATIONS

European Search Report dated Aug. 6, 2012 which was issued in connection with the EP Application No. 12161189.1 which was filed on Mar. 26, 2012.

*Primary Examiner* — Michael Carey
*Assistant Examiner* — Don N Ho

(57) ABSTRACT

A sensor for measuring a concentration of a respiratory gas component is disclosed herein. The sensor comprises at least one radiation source configured to emit radiation and at least one radiation sensing detector configured to receive radiation and provide a signal indicative of the concentration of the gas component. The sensor further comprises an electronics board configured to receive and process the signal to determine the concentration, and an energy storage device configured to supply energy to the radiation source. The electronics board is configured to choose from among at least two different modes, one being an operation mode allowing sufficient energy supply to the radiation source, and another being a rest mode allowing reduced energy supply compared to the operation mode to limit radiation for saving energy within the breathing cycle. A gas analyzer and method for measuring a concentration of a respiratory gas component are also provided.

19 Claims, 3 Drawing Sheets

(51) Int. Cl.
   *A61B 5/091* (2006.01)
   *A61B 5/00* (2006.01)
   *A61B 5/08* (2006.01)
   *A61M 16/08* (2006.01)
   *A61M 16/10* (2006.01)
   *A61M 16/00* (2006.01)

(52) U.S. Cl.
   CPC .... *A61M 16/0816* (2013.01); *A61M 16/0858* (2014.02); *A61B 2560/0209* (2013.01); *A61B 2562/0233* (2013.01); *A61M 16/1055* (2013.01); *A61M 16/1065* (2014.02); *A61M 2016/0033* (2013.01); *A61M 2016/103* (2013.01); *A61M 2016/1025* (2013.01); *A61M 2205/3306* (2013.01); *A61M 2205/3569* (2013.01); *A61M 2205/3592* (2013.01); *A61M 2230/432* (2013.01); *A61M 2230/435* (2013.01)

(56) References Cited

U.S. PATENT DOCUMENTS

| | | | | |
|---|---|---|---|---|
| 2009/0247849 | A1* | 10/2009 | McCutcheon | A61B 5/14551 600/323 |
| 2011/0162647 | A1* | 7/2011 | Huby | A61M 16/0057 128/203.14 |
| 2012/0016251 | A1* | 1/2012 | Zhang | A61B 5/0402 600/532 |

FOREIGN PATENT DOCUMENTS

| | | |
|---|---|---|
| EP | 2062531 A1 | 5/2009 |
| GB | 2375609 A | 11/2002 |
| WO | 2006080856 A1 | 8/2006 |
| WO | 2007002389 A2 | 1/2007 |

* cited by examiner

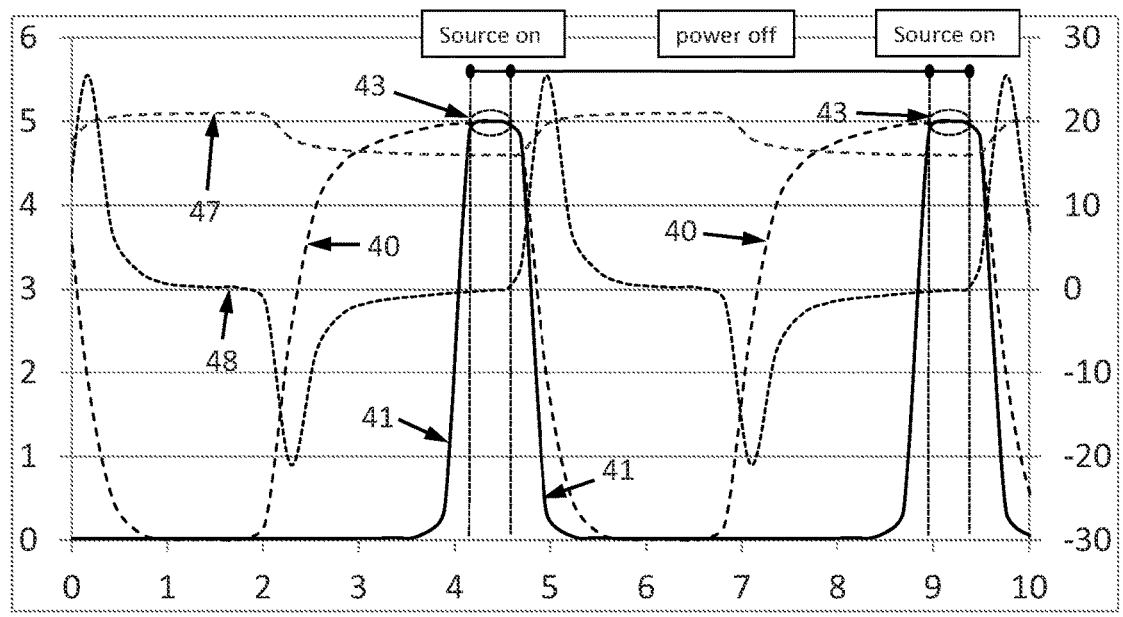

SENSOR, GAS ANALYZER AND METHOD FOR MEASURING CONCENTRATION OF AT LEAST ONE RESPIRATORY GAS COMPONENT

BACKGROUND OF THE INVENTION

Embodiments of the present invention relate to a sensor, gas analyzer and method for measuring a concentration of at least one respiratory gas component in a breathing gas, with varying concentration during a breathing cycle comprising an inspiration phase, an expiration phase and a phase between the inspiration and expiration.

Patients that are health monitored are usually connected to a host, such as a patient monitor. Patient monitors may include electrical cables or plastic tubing that transmit measurement samples or data from sensors attached to patient. Data and samples are usually analyzed at the host and showed on the host's display for the care giver. Cables and tubes between the patient and the host generate different problems for care givers as wired patient complicate care procedures and can create various risks for the patient. Such risks include tearing cables and tubes which may hurt and disturb the patient. While wireless sensors may decrease these problems and risks, the size, weight and operating time cause other types of problems.

To ensure good usability and functionality of breathing gas analyzers, such as a mainstream type analyzer placed close to a patient's airways into the end of the endotracheal tube, mask or prongs, it is important that the device size is small, especially with smaller patients, to ensure that the device would not prevent clinical procedures by covering critical areas of a patient's face or body. The device should also be lightweight in order to ensure that the device would not, for example, bend an endotracheal tube which could clog the air flow between the lungs and the ventilator or that the device would not unfasten from a patient's nasal or oral cavities if mask or prongs are used.

Short operating time is one of the challenges in transportable wireless gas analyzing due to the electrical power consumption of the gas analyzer. This is especially a problem with gas analyzing based on gas absorption at infrared radiation wavelengths, which is the most common and functioning real-time method in analyzing the concentration of most common gases. The most power consuming component in such an analyzer is the radiation source that generates the infrared radiation wave lengths. Optical reflector and collimator designs may increase the emitted signal efficiency few times higher, but the electrical power consumed by the radiation source still varies between approximately 1 W-1.5 W. The energy density of rechargeable lithium-ion batteries are between 150-250 Wh/l, which is one of the best, commercially available, rechargeable battery technologies at the moment. With these given values, a wireless analyzer comprising a large rechargeable battery with a size such as 100 $cm^3$ (1 dl) would function continuously for approximately 10-25 hours. This short operating time, together with the large battery size of 100 $cm^3$, creates a heavy analyzer and makes it difficult to treat adults and smaller patients.

BRIEF DESCRIPTION OF THE INVENTION

In accordance with an embodiment of the present invention, a sensor is provided for measuring a concentration of at least one respiratory gas component in a breathing gas with varying concentrations during a breathing cycle having an inspiration phase, an expiration phase and a phase between the inspiration and expiration. The sensor comprises at least one radiation source configured to emit radiation, and at least one radiation sensing detector configured to receive radiation and provide a signal indicative of the concentration of the at least one respiratory gas component. The sensor further comprises an electronics board configured to receive and process the signal from the at least one radiation sensing detector to determine the concentration of the at least one respiratory gas component, and an energy storage device for supplying energy to the at least one radiation source. The electronics board is configured to choose from at least two modes of energy supply to the at least one radiation source. In one mode, an operation mode is configured to allow sufficient energy supply to at least one radiation source needed for subsequent concentration determination within at least one phase of the breathing cycle. In another mode, a rest mode is configured to allow reduced energy supply to at least one radiation source compared to the operation mode, to limit radiation for conserving energy from the energy storage device within the breathing cycle.

In accordance with an embodiment of the present invention, a gas analyzer is provided for measuring a concentration of at least one respiratory gas component in a breathing gas with varying concentrations during a breathing cycle having an inspiration phase, an expiration phase and a phase between the inspiration and expiration. The gas analyzer comprises an airway adapter comprising a sampling cell configured to allow breathing gas flow, at least one optical component configured to guide radiation, wherein the optical component is in direct or indirect contact with the respiratory gas inside the sampling cell, a first port configured to deliver respiratory gas to the sampling cell, and a second port configured to remove respiratory gas from the sampling cell. The gas analyzer further comprises a sensor connectable to the airway adapter, wherein the sensor comprises at least one radiation source configured to emit radiation towards the at least one optical component, at least one radiation sensing detector configured to receive and provide a signal indicative of the concentration of the at least one respiratory gas component, an electronics board configured to receive and process the signal from the at least one radiation sensing detector to determine the concentration of at least one respiratory gas component, and an energy storage device configured to supply energy to the at least one radiation source. The electronics board is configured to choose from at least two different modes of energy supply to at least one radiation source. In one mode, an operation mode is configured to allow sufficient energy supply to the at least one radiation source needed for subsequent concentration determination within at least one phase of the breathing cycle. In another mode, a rest mode is configured to allow reduced energy supply to the at least one radiation source compared to the operation mode, to limit radiation for conserving energy of the energy storage device within the breathing cycle, when reduced accuracy in concentration is acceptable.

In accordance with an embodiment of the present invention, a method is provided for measuring a concentration of at least one respiratory gas component in a breathing gas with varying concentrations during a breathing cycle having an inspiration phase, an expiration phase and a phase between the inspiration and expiration. The method comprises emitting radiation using at least one radiation source towards at least one optical component in direct or indirect contact with the respiratory gas inside a sampling cell. The method further comprises receiving the radiation in the at least one radiation sensing detector and providing, from the at least one radiation sensing detector, a signal indicative of the concentration of the at least one respiratory gas component. The method further comprises receiving the signal from the at least one radiation sensing detector and processing the signal in an electronics board to determine the concentration of at least one respiratory gas component, and supplying energy from an energy storage device to the at least one radiation source. The method further comprises choosing the electronics board from among at least two different modes of energy supply to the at least one radiation source. In one mode, an operation mode is configured to allow sufficient energy supply to at least one radiation source needed for subsequent concentration determination within at least one phase of the breathing cycle. In another mode, a rest mode is configured to allow reduced energy supply to the at least one radiation source compared to the operation mode, to limit radiation for saving energy of the energy storage device within the breathing cycle.

BRIEF DESCRIPTION OF THE DRAWINGS

FIG. 5 is a carbon dioxide concentration curve measured in an operation mode, a carbon dioxide concentration curve measured in a rest mode, an oxygen concentration curve and a derivative of oxygen concentration, when the measurements were made with the gas analyzer and sensor in FIG. 1 as a function of time in accordance with an embodiment of the present invention.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
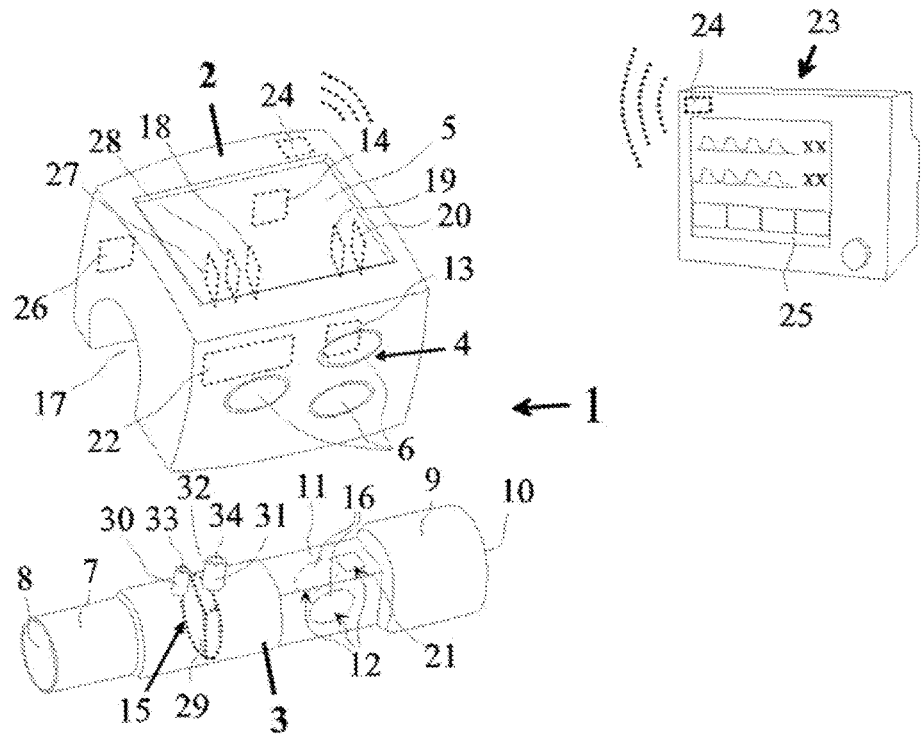
FIG. 1 is a schematic view of a gas analyzer and a sensor in a communication with a host device in accordance with an embodiment of the present invention.

FIG. 1 shows a portable breathing gas analyzer 1 comprising a sensor 2 and airway adapter 3 which is connectable to the sensor 2. The sensor 2 may also comprise a display 5 that can show the measured breathing gas values for the user as numbers, but in waveforms as well. The sensor 2 may also comprise a user interface 4, such as buttons 6, In an embodiment of the present invention, a touch screen can replace the buttons 6 for the user to operate the sensor.

Electrical power to operate the sensor can be delivered from an energy storage device 22, such as a single use or rechargeable battery. The gas analyzer can communicate wirelessly with other devices or host devices 23 such as a patient monitor through radio frequency transceivers 24 placed inside the sensor 2 and the host device 23. Host devices such as the patient monitor can show measured values and waveforms from its display 25 in a similar manner as the gas analyzer 1 shows values on its display 5. When the wireless operation is not necessary and when the energy level of the rechargeable energy storage device 22 is low and needs to be recharged, the analyzer 1 or the sensor 2 can be connected to the host device 23 through an electrical cable to transmit electrical power, as well as measured values. It is also possible to replace the rechargeable energy storage devices such as batteries with new or recharged batteries to enable continuous use of the gas analyzer when any of the host devices are present.

The sensor 2 further comprises at least one radiation source 13, such as an infrared radiation source, to emit radiation, and at least one radiation sensing detector 14 to receive the radiation emitted by at least one radiation source. An electronics board 26 is part of the sensor, too, receiving and processing the signal from the at least one radiation sensing detector 14 to determine the concentration of the at least one respiratory gas component of the breathing gas. The sensor 2 may further comprise a flow detector 27 configured to provide a signal indicative of the flow of the breathing gas to the electronics board 26, and a pressure detector 28 configured to provide a signal indicative of the pressure of the breathing gas to the electronics board 26. The electronics board may further comprise a CPU to control the different functions of the sensor and to process measurement data from different signal sources into the form of numbers and waveforms to be shown for the care giver on the display at the sensor or at the host where the data can be transmitted wirelessly.

The sensor 2 may further comprise an oxygen detector 18 providing a signal indicative of the oxygen in the breathing gas. The oxygen detector 18 can be for example fuel cell or polarographic type technology, but can be implemented with other technologies as well. In an embodiment of the present invention, the sensor 2 may comprise a radiation source 19 and a radiation sensing detector 20 based on, for example, fluorescence quenching providing a signal indicative of the oxygen in the breathing gas.

The airway adapter 3 comprises a first port 7 with a first opening 8 to deliver the respiratory gas to the sampling cell, wherein the first port can be connected to an endotracheal tube, nasal mask, facial mask or similar equipment that is further connected to the patient and a second port 9 with a second opening 10 to remove the respiratory gas from the sampling cell. The second port can be connected to for example a ventilator circuit, resuscitator or similar when the patient is intubated or it can be left non-connected if the sensor 2 is connected to nasal or facial mask or similar. The first opening 8 and the second opening 10 allow the fresh breathing gas to flow through the airway adapter into the patient's lungs and the used breathing gas to flow out from the patient's lungs through the airway adapter.

The airway adapter further comprises a sampling cell 11 configured to allow the breathing gas to flow. The sampling cell 11 is also configured to measure gas concentration(s) of breathing gases. The sampling cell comprises at least one optical component 12 for guiding the radiation, wherein guiding may comprise conveying, passing, or reflecting the radiation. The optical component may be in direct or indirect contact with the respiratory gas inside the sampling cell. The optical component 12 may be at least one optical window 16 to convey or pass a radiation, such as an infrared radiation, through the sampling cell perpendicularly through the breathing gas flowing in the airway adapter. In an embodiment of the present invention where there are two optical windows, the optical windows may be located on both sides of the sampling cell. The measurement is enabled when the airway adapter 3 is connected to a connecting point 17 of the sensor 2, when the at least one radiation source 13, the at least one optical window 16 and the at least one radiation sensing detector 14 are aligned so that the radiation from the at least one radiation source 13 can pass through the at least one optical window 12, and through the breathing gas, into the at least one radiation sensing detector 14.

In an embodiment of the present invention, the airway adapter 3 may comprise a flow measuring component 15 configured to measure flow, such as a flow barrier 29 with pressure ports 30, 31, for measuring the breathing gas flow between the first port 7 and the second port 9 and a pressure measuring component 32, such as a port for measuring the pressure of the breathing gas between the first port 7 and the second port 9. As shown in FIG. 1 the pressure measuring component 32 may comprise one of the pressure ports 30, 31 or a separate port.

The flow detector 27 for measuring the flow can be for example one of the known technologies such as a differential pressure measurement through the pressure ports 30, 31 over the flow barrier 29. In an embodiment of the present invention, the flow measurement can be based on hot wire or ultrasonic transducer technology. The pressure detector 28 for measuring the pressure can be made by comparing the breathing gas pressure through one of the pressure ports 30, 31 with the outside pressure. FIG. 1 shows the flow measurement over the flow barrier 29 located in airway adapter 3 that comprises the pressure ports 30 and 31 with pressure openings 33 and 34 to allow pressure and pressure differences proportional to flow of breathing gas to be measured over the flow barrier 29 inside the airway adapter 3 through the pressure openings 33 and 34. The measurement is enabled when the airway adapter 3 is connected to the connecting point 17 of the sensor 2 and when the pressure openings 33 and 34 connect with the flow detector 27 and the pressure detector 28 located inside the sensor 2. The pressure openings 33 and 34 may comprise filters (not shown in figures) to prevent bacteria and viruses to enter through the ports into the flow detector 27 and the pressure detector 28.

The oxygen detector 18, for example fuel cell type or polarographic type detector used for measuring the concentration of oxygen in the breathing gas, may be located inside the sensor 2. To enable the oxygen measurement from the breathing gas, the oxygen detector is in fluid connection with the breathing gas through the opening such as the pressure opening 34 in pressure port 31 in airway adapter 3. When the airway adapter 3 is connected to sensor 2 the fluid connection through the opening 34 between the breathing gas and the oxygen detector 18 is established.

In an embodiment of the present invention, the airway adapter 3 comprises additional optical components for gas concentration measurement to measure gases that are insensitive to infrared radiation such as oxygen. The optical component 12 may comprise a luminophore coated surface, where the component may be transparent to radiation and is able to guide and convey radiation. When the radiation emitted by the radiation source towards the optical component meets the luminescable material in contact with the respiratory gas, such as oxygen, luminescent radiation is generated indicative of oxygen concentration of the respiratory gas and received by the detector. In this embodiment of the present invention, the optical component may be in indirect contact with the respiratory gas. The luminescent radiation may be guided through the optical component or away from the surface of the optical component.

As an example in FIG. 1 the concentration of oxygen in the breathing gas can be measured based on the fluorescence quenching, where the radiation source 19 directs the radiation towards the optical component 12, such as a fluorescence quenching element 21, which is in contact with the breathing gases, enabling the fluorescence quenching based oxygen measurement indicative of the oxygen in the breathing gas, which emits radiation proportional to the oxygen content in the gas directing it towards the optical component 12 and radiation sensing detector 20.

Some hospitals and users prefer disposable airway adapters, but also other breathing circuit accessories are made disposable to reduce contamination risk. Patient's lungs generate mucus and other secretions and injured lungs bleed blood, which easily enter the breathing circuit accessory forming a good environment for bacteria and viruses to survive and reproduce. To minimize the contamination risk a disposable accessory need to be changed and reusable accessory to be cleaned frequently enough. Thus sensible and costly flow and pressure detectors are better to locate inside the sensor 2 to avoid cleaning and to make them reusable.

When the patient is in stable condition it is usually sufficient to show only the end tidal (ET) values of gas concentrations such as carbon dioxide ($CO_2$) and oxygen ($O_2$). There may be need for showing fraction of inspired values (FI) in addition to ET-values or the accurate real time waveforms or capnogram if the condition of the patient changes rapidly or for some other clinical reason. ET-value of certain breathing gas is the maximal value of the concentration of that gas. FI-value is the concentration of a gas participating in gas exchange in the alveoli. The I:E ratio defines the ratio of the duration of inspiration to the duration of expiration. A range of 1:1.5 to 1:2 for an adult is considered acceptable for mechanical ventilation. Ratios of 1:1 or higher may cause hemodynamic complications, whereas ratios lower than 1:2 indicate lower mean airway pressure and fewer associated hazards.

The radiation source 13 used in detecting gases at radiation wavelengths, such as infrared radiation wavelengths, is one of the most power consuming electrical components in the gas analyzer 1 or the sensor 2 that has a big impact on the operation time of the gas analyzer 1. The operation time can be increased by increasing the size or the energy density of the energy storage device, but a gas analyzer with small size and weight is preferred because the analyzer is placed close to the patient's mouth and should disturb the patient as little as possible.

Figure 2:
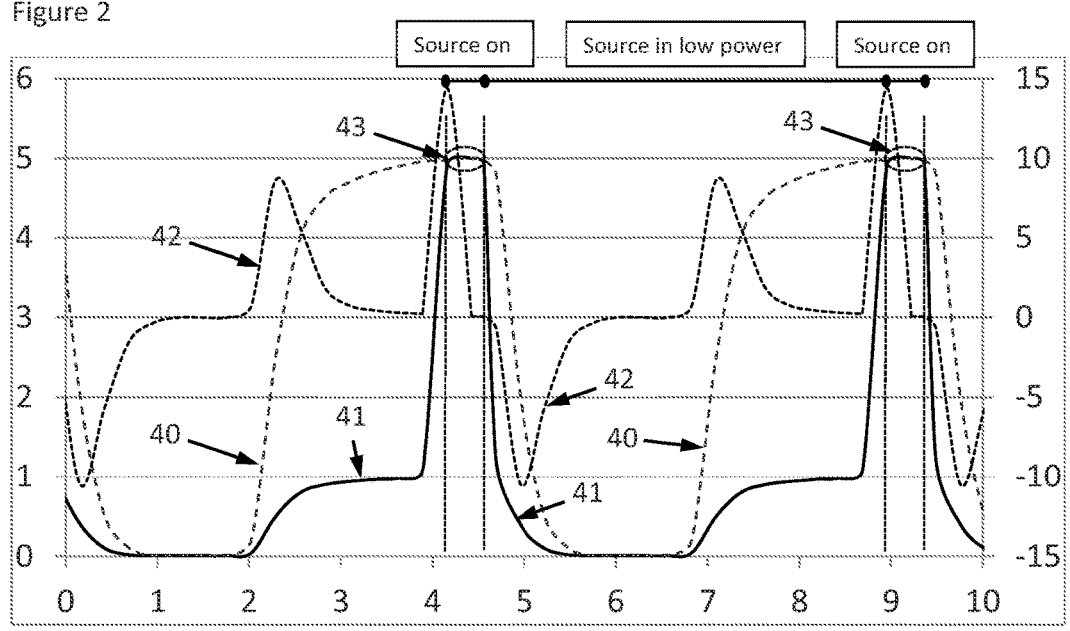
FIG. 2 is a carbon dioxide concentration curve measured in an operation mode, a derivative of the carbon dioxide concentration and a carbon dioxide concentration measured in a rest mode, when the measurements were made with the gas analyzer and sensor in FIG. 1 as a function of time in accordance with an embodiment of the present invention.

FIG. 2 shows a curve 40, which is a real-time gas concentration value or capnogram of carbon dioxide ($CO_2$) measured with a mainstream type gas analyzer 1 as described hereinbefore. The duration of inspiration is approximately 2 seconds and the duration of expiration is approximately 3 seconds. The I:E ratio is thus 1:1.5 and the respiration rate (RR) is approximately 12 breaths/minute, which is fairly normal breathing for an adult. The capnogram is generated from electrical signals from the at least one radiation sensing detector 14 that measure the infrared radiation traversing through breathing gases in the sampling cell 11 of the airway adapter 3, in this case carbon dioxide, which absorbs radiation proportional to its concentration. The infrared radiation is generated with the at least one radiation source 13, which electrical power consumption is approximately 1 watt, if it is kept constant to get uniform capnogram like a curve 40 in FIG. 2. To keep the analyzer size reasonable for usability and functional reasons the size of the energy storage device 22 should be as small as possible, for example less than 2 cm$^3$. The amount of energy stored into such device, using for example lithium-ion technology, would be around 0.4 Wh. The operating time for the gas analyzer would then be around half an hour, which is not enough even for instantaneous transport.

One way to decrease electrical power consumption of the gas analyzer 1, to lengthen the operation time and to minimize the size of the energy storage device, is to choose from among at least two different modes of energy supply to the at least one radiation source. One of the modes is an operation mode, such as a normal operating power mode, allowing sufficient energy supply to the at least one radiation source needed for subsequent concentration determination within at least one phase of the breathing cycle. The breathing cycle includes an inspiration phase, an expiration phase and a phase between the inspiration and the expiration. Another of the modes is a rest mode, such as a lower power mode, allowing reduced energy supply to the at least one radiation source compared to the operation mode to limit radiation for saving energy of the energy storage device within the breathing cycle when reduced accuracy in concentration determination is acceptable, which means that for example concentration determination can be avoided or the accuracy can be decreased.

The reduced energy supply during the rest mode may be approximately between at least 50% less than during the operation mode or approximately at least 90% less than during the operation mode. This means that the radiation source can even be turned off or if desired to adjust it into a lower power consumption mode within at least one phase of the breathing cycle. The electronics board 26 may choose the operation mode, when the phase of the breathing cycle includes at least part of the expiration or at least an end tidal volume of the expiration. Instead the electronics board may choose the rest mode within the inspiration phase and within the phase between the inspiration and expiration, but, if desired, to choose the rest mode also within the expiration phase excluding a plateau period when an end tidal volume of the expiration exists in which case the electronics board may choose the operation mode. In an embodiment of the present invention, the electronics board may choose the operation mode to measure end-tidal values of gas concentrations and to measure also only a fraction of inspired values. This may mean that the rest mode can be chosen during the rest of time required by the breathing cycle. Typically the first time period, when the operation mode is valid, is shorter than a second time period, when the rest mode is valid. The decision when the operation mode and the rest mode is chosen can be based on different available and measureable breathing gas signals such as carbon dioxide, oxygen, flow, pressure etc.

If the gas concentration, such as carbon dioxide or any other radiation source dependent signal, is the only measurable and available signal, the radiation source cannot be turned off by choosing the rest mode since the triggering signal for making the decision to turn the source back on would otherwise be lost. The gas concentration of carbon dioxide measured with constant power in the operation mode is represented by curve 40 in FIG. 2. The energy supply to the radiation source is allowed in the rest mode, but is below the amount of energy supplied during the operation mode. A curve 41 shows the gas concentration measured in the rest mode during the inspiration, the period between the inspiration and expiration, and the expiration excluding the end tidal volume of the expiration when the operation mode is valid and when the gas concentration represented by curve 41 undergoes a sudden increase and, after a short period, goes suddenly down.

The decision of when the radiation source is turned on and when it is turned into a lower power consumption mode may be based on the derivative of the real-time carbon dioxide concentration curve 42 as shown in FIG. 2. The derivative of the gas concentration gives a value relative to how fast the gas concentration is changing. When the derivative of the concentration is zero the concentration stays constant, when the derivative is less than zero the concentration decreases, and when the derivative is more than zero the concentration increases. The higher or lower the value of derivative, the faster is the change of concentration. The derivative is zero or close to zero at the plateau 43 of expiration, where the maximal gas concentration value or ET-value should be measured as shown in FIG. 2. Alternatively, the derivative would also be zero or close to zero when the gas concentration reaches its minimum during inspiration. Thus the plateau 43 at the end of expiration, where the gas concentration should be measured, can be found when the derivative returns back to zero or close to zero after a positive derivative peak caused by the exhale of gases, transition from inspiration to expiration when the gas concentration changes. When the derivative reaches zero or a value close to zero the radiation source is turned on by choosing the operation mode to enable adequate signal levels for gas concentration analyzes to obtain an ET-value. However, the measured gas concentration signal rises to a new level proportional to added radiation power, and at the same time, the concentration signal rises due to exhaled gas. For that reason there would be another positive peak in derivative proportional to concentration signal change describing that it cannot be used for analyzing purposes yet. After the peak, when the derivative returns back to zero or a value close to zero, the maximal concentration or ET-value can be measured.

As the gas concentration starts to decrease at the end of expiration and the derivative decreases to a level below zero, the radiation source can be converted to the rest mode again to save electrical energy. The gas concentration signal decreases proportional to decreased radiation and the amplitude of its derivative decreases as well. The lowest radiation power that can be used depends on the lowest signal to noise ratio that can be used to reliably detect the start of a normal operating mode to turn on the radiation source again to its normal operating power in order to obtain end tidal gas concentration values. When the source is turned into the rest mode the amplitude of derivative decreases proportionally. In an embodiment of the present invention, it is possible to scale and filter the derivative with a value inversely proportional to radiation decrease to obtain more reliable signals for decision making purposes. However, this will limit the highest possible respiration rates (RR). When the radiation source is turned on only for the time of plateau, for $\frac{1}{10}^{th}$ of the time and otherwise it is turned into the rest mode, such as $\frac{1}{5}^{th}$ of the electrical power in normal operation mode, as shown in FIG. 2, the electrical power consumption of the radiation source can be decreased approximately by 75%, for example from 1 W to 0.25 W.

In infrared radiation based gas absorption measurement the gas concentration measurement resolution and the signal to noise ratio are better at lower gas concentration values and decrease towards higher concentrations. With appropriate radiation source supply energy during the rest mode, which occurs mainly during the inspiration and when the gas concentration values should be close to zero, it is also possible to measure the fraction of inspired (FI) gas concentration values to get understanding and to ensure that the patient is really breathing the fresh gas into the lungs. If the radiation source supply energy is turned off, the fraction of inspired gas concentration measurement during the rest mode is also turned off.

Figure 3:
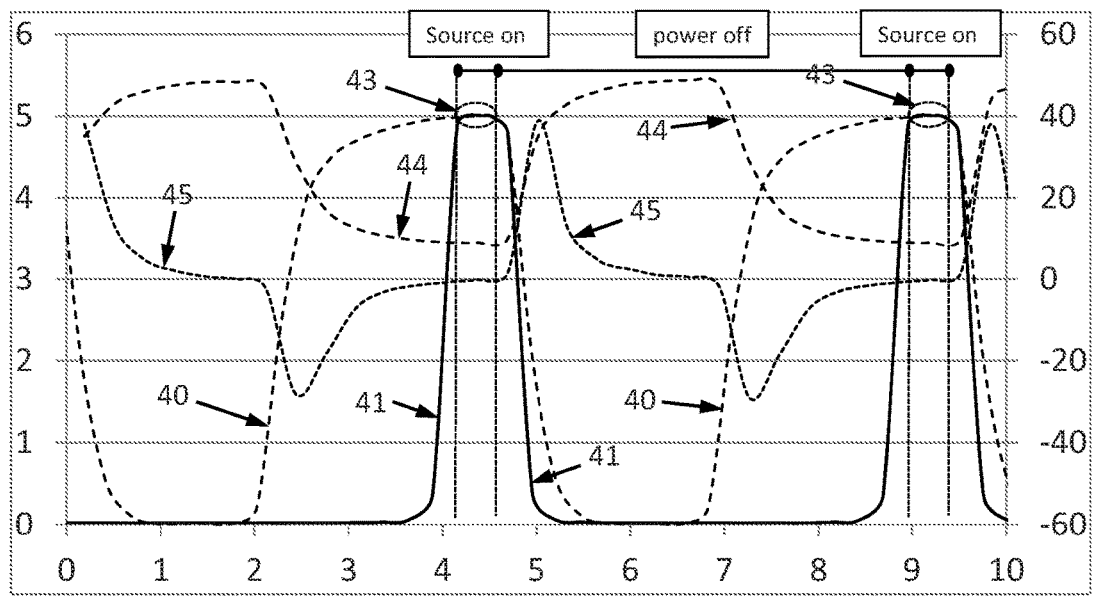
FIG. 3 is a carbon dioxide concentration curve measured in an operation mode, a carbon dioxide concentration curve measured in a rest mode, a pressure curve and a derivative of the pressure, when the measurements were made with the gas analyzer and sensor in FIG. 1 as a function of time in accordance with an embodiment of the present invention.

In an embodiment of the present invention, it is possible to obtain the fraction of inspired (FI) gas concentration values by switching to the normal operating mode during the inspiration phase. However, this will increase the supply power consumption depending on how long the period of normal operating mode is. The decision when the normal operating mode is switched on during the rest mode during inspiration can be based on the signal sources similar to those as described earlier for the carbon dioxide. For example, if the breathing circuit pressure is used as a signal source, as shown in FIG. 3, the normal operating mode can be switched on when the derivative of the pressure is close to zero after a positive derivative peak, which describes the start of inspiration. Similarly the normal operating mode can be turned back to rest mode to save supply energy when the derivative of pressure starts to decrease from the value close to zero. Thus, the time of normal operating mode during the inspiration phase locates to the end of inspiration when the gas concentration value should be the lowest and the most reliable and the period of time would be similar to that of during expiration depending on the switching window, the lower and upper limit of derivative close to zero.

In an embodiment of the present invention, the radiation source can be turned on by choosing the operation mode to get ET-values and turned off by choosing the rest mode during the rest of the time to save electrical energy when the decision is based on the pressure measurement of the breathing gases as is the case in FIG. 3. If the breathing gas pressure is measured the continuous pressure curve 44 in FIG. 3 looks similar to gas concentration capnogram curve 40 in the operation mode also shown in FIG. 3, but is shifted 180° degrees in phase. The decision of when the radiation source is turned on and off using the electronics board 26 can be based on the real-time gas pressure curve 44 as shown in FIG. 3. At the end of exhalation, when the radiation source is turned on by means of the electronics board 26 and as the pressure starts to increase again as inspiration starts the radiation source 13 is turned off again, the gas pressure reaches its minimum values. The disadvantage is the pressure offset needed inside the breathing circuit that keeps the patient's lungs open during all times and prevents the alveoli from collapsing, which means that the pressure will not reach zero values at any point, but rather drifts a long time causing inaccuracy into radiation source control.

The derivative of the real-time gas pressure curve 45 as shown in FIG. 3 can be used by the electronics board 26 to turn on and off the radiation source 13. FIG. 3 illustrates a carbon dioxide gas concentration curve 41 measured in the rest mode during the inspiration, the period between the inspiration and expiration, and the expiration excluding the end tidal volume of the expiration when the operation mode is valid and when the gas concentration curve 41 goes suddenly up and after a short period goes suddenly down. In this embodiment, the energy supply to the radiation source 13 is zero. The carbon dioxide gas concentration curve 40 is measured in the operation mode. The derivative of the gas pressure gives a value relative to how fast the pressure is changing. When the derivative of the pressure is zero the pressure stays constant, when the derivative is less than zero the pressure decreases, and when the derivative is more than zero the pressure increases. The higher or lower the value of derivative, the faster is the change of pressure. The derivative of the gas pressure is zero or close to zero when the gas pressure is at its minimum at the end of expiration, when the maximal gas concentration value or ET-value should be measured at the plateau 43 of expiration as shown in FIG. 3. Alternatively, the derivative is zero or close to zero when the gas pressure reaches its maximum during inspiration. Thus the plateau 43 at the end of expiration, where the gas concentration should be measured, can be found always when the derivative returns back to zero or close to zero after a negative peak of derivative caused by a pressure drop during exhale of gases. When the derivative reaches zero or a value close to zero the radiation source 13 is turned on to its normal operating power to enable adequate signal levels for gas concentration analyzes to get ET-value. When the derivative starts to increase and go above zero, as the gas pressure starts to increase when inspiration starts, the radiation source can be turned off to save electrical energy. When the radiation source is turned on only for the time of plateau 43, approximately for $1/10^{th}$ of the time and otherwise it is turned off, as shown in FIG. 3, the electrical power consumption of the radiation source can be decreased approximately 90%, for example from 1 W to 0.1 W.

The pressure curve 44 measured by the pressure detector 28 and its derivative curve 45 can also be combined to turn on and off the radiation source by means of the electronics board 26. The time when the radiation source 13 is turned on may be due to combination when the pressure is close to its minimum value and its derivative is close to zero within some predetermined limits. The radiation source is turned off again when the pressure and its derivative start to rise again.

Figure 4:
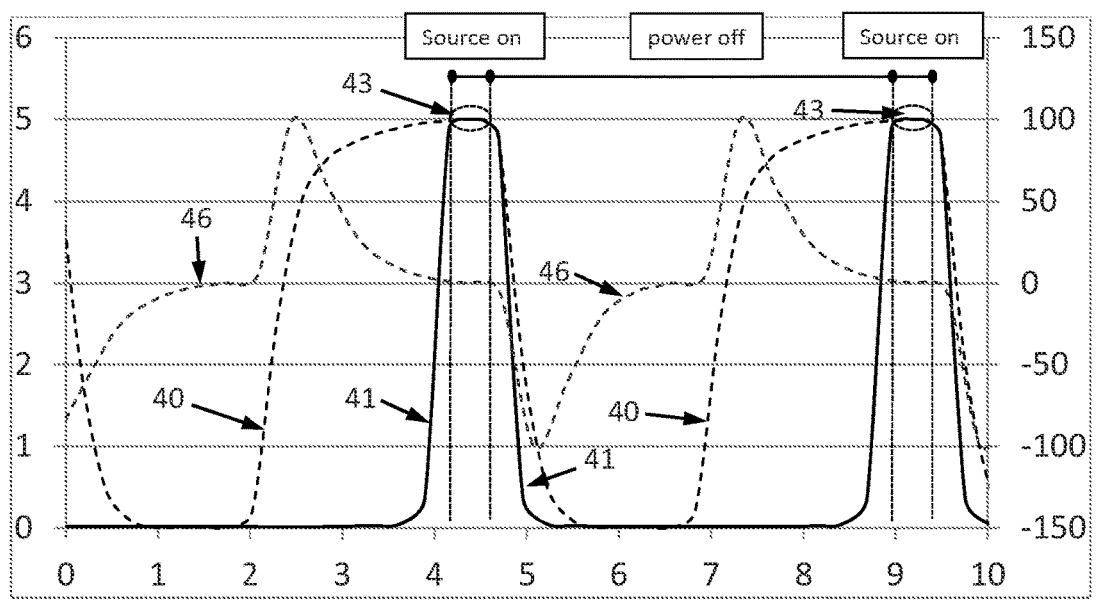
FIG. 4 is a carbon dioxide concentration curve measured in an operation mode, a carbon dioxide concentration measured in a rest mode, and a flow curve, when the measurements were made with the gas analyzer and sensor in FIG. 1 as a function of time in accordance with an embodiment of the present invention.

If the decision of when the radiation source 13 is turned on and off is based on the breathing gas flow curve 36 measured by the flow detector 27 as shown in FIG. 4, the radiation source should be turned on during expiration, when the expiration flow closes the zero (no flow) after the maximum flow and turned off again when the flow turns to negative. In an embodiment of the present invention, the derivative of flow signal (not shown in FIG. 4) can be combined with the actual flow signal similarly as described with pressure signals, but the flow signal should already be fairly accurate for making a decision whether to turn on or off the radiation source and can be useful alone. FIG. 4 illustrates the carbon dioxide concentration curve 41 measured partly in the rest mode and partly in the operation mode just as explained when referring to FIG. 3, the carbon dioxide concentration curve 40 measured in the operation mode and the plateau 43, too.

In an embodiment of the present invention, other signal sources can be used for decision making in the electronics board 26 to determine whether or not the radiation source 13 should be turned on or off. If for example oxygen measuring device or similar is available oxygen concentration curve 47, as shown in FIG. 5, is in 180° degree phase shift compared to the carbon dioxide gas concentration curve 40 measured in the operation mode as shown in F FIG. 5. This means that carbon dioxide will be at its maximum during expiration, but oxygen will be at its minimum. As oxygen is measured with another measurement technology than gases based on absorption of infrared radiation wave lengths, its signal can be used to turn on and off the radiation source to save electrical energy similarly as previously described in respect to gas pressure and its derivative. This is true where another oxygen measurement technology uses less energy than typical radiation source. Chemical oxygen sensors need less energy, or can function without energy, than sensors with a radiation source. In addition, the derivative of oxygen concentration curve 48 can be used by the electronics board to turn on and off the radiation source 13. The carbon dioxide concentration curve 41 in FIG. 5 was measured partly in the rest mode and partly in the operation mode as explained when referring to FIG. 3 and FIG. 4.

The breathing gas measurements such as pressure, flow or oxygen based on, for example, fuel cell or polarography technologies, are less power consuming and can therefore be operated continuously without consuming excessive supply energy from the energy storage device. These measurements can be used as signal sources to switch the more power consuming measurements between the normal operating mode and the rest mode, such as gas concentration measurement based on infrared radiation wavelengths or the oxygen measurement based on fluorescence quenching that may be more power consuming measurement as well. The switching logic to operate for example the fluorescence quenching based oxygen measurement between the normal operating mode and the rest mode would be similar to that of gas concentration measurements at infrared radiation wavelengths, but with the phase shift of 180° compared to for example carbon dioxide. Thus the oxygen measurement indicative of the oxygen in the breathing gas can be switched between the operating mode and the rest mode based on the derivative of the oxygen concentration signal where in the rest mode and the radiation source is not turned off, but it is adjusted to lower supply power to ensure continuous derivative of oxygen concentration for decision making of the mode. Similarly for example the breathing gas pressure and the flow, as described previously for carbon dioxide, can be used to switch power supply modes, by noting the 180° phase shift in regard to carbon dioxide.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A sensor for measuring a concentration of at least one respiratory gas component in a breathing gas, which concentration is varying during a breathing cycle having an inspiration phase, an expiration phase and a phase between the inspiration and expiration, the sensor comprising:
    at least one radiation source configured to emit radiation;
    at least one radiation sensing detector configured to receive radiation and provide a signal indicative of the concentration of the at least one respiratory gas component;
    an electronics board configured to receive and process the signal from the at least one radiation sensing detector to determine the concentration of the at least one respiratory gas component; and
    an energy storage device configured to supply energy to the at least one radiation source;
    wherein the electronics board is configured to choose from at least an operation mode providing sufficient energy supply to the at least one radiation source for subsequent concentration determination during a first time period, and a rest mode providing a reduced energy supply to the at least one radiation source during a second time period, wherein the operation mode is chosen when a derivative of a concentration of the at least one respiratory gas component approaches zero after a positive derivative peak, and the rest mode is chosen when the derivative decreases to a level below zero.

2. The sensor according to claim 1, wherein the electronics board is configured to choose the operation mode when the phase of the breathing cycle comprises one of at least part of the expiration and at least an end tidal volume of the expiration, and the electronics board is configured to choose the rest mode within one of the inspiration phase and the phase between the inspiration and expiration.

3. The sensor according to claim 1, wherein the electronics board is configured to choose the rest mode within the expiration phase excluding a plateau period when an end tidal volume of the expiration exists in which case the electronics board is configured to choose the operation mode.

4. The sensor according to claim 1, wherein the electronics board is configured to choose the operation mode to measure end-tidal values of gas concentrations and a fraction of inspired values, and configured to choose the rest mode during a portion of the time required by the breathing cycle when reduced accuracy in concentration determination is acceptable, and wherein a time period when the operation mode is valid is shorter than a time period when the rest mode is valid.

5. The sensor according to claim 1, further comprising at least one of a display configured to show breathing gas values measured, a user interface configured to operate the sensor, and a radio frequency transceiver configured to communicate with a host device.

6. The sensor according to claim 1, wherein at least one respiratory gas component is one of carbon dioxide and oxygen and the at least one radiation source emits radiation towards the breathing gas to measure the concentration of one of carbon dioxide and oxygen.

7. The sensor according to claim 1, wherein in the rest mode when reduced energy is configured to be supplied to the at least one radiation source, the at least one radiation source is configured to be either turned off, wherein at least one of (i) the electronics board is configured to pause energy supply to the at least one radiation source, and (ii) the at least one radiation source is configured to receive less energy than in the operation mode, but more than pausing energy supply where the electronics board is configured to adjust energy supply to the at least one radiation source to a lower operating power.

8. The sensor according to claim 1, further comprising a pressure detector configured to provide a signal indicative of the pressure of the breathing gas to the electronics board wherein the operation mode is chosen when a derivative of a the pressure approaches zero after a positive derivative peak in order to measure a fraction of inspired gas concentration values, and the rest mode is chosen when the derivative of the pressure decreases to a level below zero.

9. A gas analyzer for measuring a concentration of at least one respiratory gas component in a breathing gas, which concentration is varying during a breathing cycle having an inspiration phase, an expiration phase and a phase between the inspiration and expiration, the gas analyzer comprising:
  an airway adapter comprising a sampling cell configured to allow the breathing gas flow, at least one optical component configured to guide radiation, wherein the optical component is in direct or indirect contact with the respiratory gas inside the sampling cell, a first port configured to deliver respiratory gas to the sampling cell, and a second port configured to remove respiratory gas from the sampling cell;
  a sensor connectable to the airway adapter, the sensor comprising at least one radiation source configured to emit radiation towards the at least one optical component, at least one radiation sensing detector configured to receive for radiation and provide a signal indicative of the concentration of the at least one respiratory gas component, an electronics board configured to receive and process the signal from the at least one radiation sensing detector to determine the concentration of the at least one respiratory gas component, and an energy storage device configured to supply energy to the at least one radiation source;
  wherein the electronics board is configured to choose from among at least an operation mode providing sufficient energy supply to the at least one radiation source for subsequent concentration determination during a first time period, and a rest mode providing a reduced energy supply to the at least one radiation source during a second time period, wherein the operation mode is chosen when a derivative of a concentration of the at least one respiratory gas component approaches zero after a positive derivative peak, and the rest mode is chosen when the derivative decreases to a level below zero.

10. The gas analyzer according to claim 9, wherein the sensor comprises at least one of a pressure detector and a flow detector, and the airway adapter comprises at least one of a pressure measuring component communicating with the pressure detector configured to provide a signal indicative of the pressure inside the airway adapter to the electronics board, and a flow measuring component communicating with the flow detector configured to provide a signal indicative of the flow through the airway adapter to the electronics board.

11. A method for measuring a concentration of at least one respiratory gas component in a breathing gas, which concentration is varying during a breathing cycle having an inspiration phase, an expiration phase and a phase between the inspiration and expiration, the method comprising:
  emitting radiation by at least one radiation source towards at least one optical component one of in direct and indirect contact with the respiratory gas inside a sampling cell,
  receiving the radiation by at least one radiation sensing detector and providing from the at least one radiation sensing detector a signal indicative of the concentration of the at least one respiratory gas component;
  receiving the signal from the at least one radiation sensing detector and processing the signal in an electronics board to determine the concentration of the at least one respiratory gas component;
  supplying energy from an energy storage device to the at least one radiation source; and
  choosing among at least an operation mode providing sufficient energy supply to the at least one radiation source for subsequent concentration determination during a first time period, and a rest mode providing a reduced energy supply to the at least one radiation source during a second time period, wherein the operation mode is chosen when a derivative of a concentration of the at least one respiratory gas component approaches zero after a positive derivative peak, and the rest mode is chosen when the derivative decreases to a level below zero.

12. The method according to claim 11, comprising choosing the rest mode within the expiration phase while excluding a plateau period when an end tidal volume of the expiration exists, and choosing the operation mode for the plateau period.

13. The method according to claim 11, comprising choosing the operation mode for measuring end-tidal values of gas concentrations and a fraction of inspired values and choosing the rest mode by the breathing cycle, and wherein a time period, when the operation mode is valid, is shorter than a time period when the rest mode is valid.

14. The method according to claim 11, comprising:
  choosing the operation mode when the phase of the breathing cycle comprises one of at least part of the expiration and at least an end tidal volume of the expiration; and
  choosing the rest mode within one of the inspiration phase and the phase between the inspiration and expiration.

15. The gas analyzer according to claim 9, wherein the electronics board is configured to choose the operation mode when the phase of the breathing cycle comprises one of at least part of the expiration and at least an end tidal volume of the expiration, and the electronics board is configured to choose the rest mode within one of the inspiration phase and the phase between the inspiration and expiration.

16. The sensor according to claim 1, wherein the first time period is shorter than said second time period.

17. The gas analyzer according to claim 9, wherein the first time period is shorter than said second time period.

18. The method according to claim 11, wherein the first time period is shorter than said second time period.

19. The sensor according to claim 1, further comprising a flow detector configured to provide a signal indicative of the flow of the breathing gas to the electronics board, wherein choosing from among at least two different modes is based on a signal from the flow detector.

\* \* \* \* \*